United States Patent
Geschwentner

[11] Patent Number: 6,011,647
[45] Date of Patent: *Jan. 4, 2000

[54] SWITCHABLE ILLUMINATION SYSTEM FOR A SURGICAL MICROSCOPE

[75] Inventor: Otto Geschwentner, Balgach, Switzerland

[73] Assignee: Leica Mikroskopie Systeme AG, Heerbrugg, Switzerland

[ * ] Notice: This patent issued on a continued prosecution application filed under 37 CFR 1.53(d), and is subject to the twenty year patent term provisions of 35 U.S.C. 154(a)(2).

[21] Appl. No.: 08/365,480

[22] Filed: Dec. 28, 1994

[30] Foreign Application Priority Data

Dec. 28, 1993 [DE] Germany .............................. 43 44 770

[51] Int. Cl.[7] ................................................... G02B 21/00
[52] U.S. Cl. ........................... 359/389; 359/385; 351/216
[58] Field of Search .................................... 359/385, 388, 359/389, 371, 377, 726, 737, 799, 386, 387, 390; 351/211, 216, 217

[56] References Cited

U.S. PATENT DOCUMENTS

| | | | |
|---|---|---|---|
| 3,798,435 | 3/1974 | Schindl | 359/388 |
| 4,148,552 | 4/1979 | Suzuki et al. | 359/388 |
| 4,505,555 | 3/1985 | Piller et al. | 359/389 |
| 4,657,357 | 4/1987 | Nishimura et al. | 359/799 |
| 4,687,304 | 8/1987 | Piller et al. | 359/387 |
| 4,843,242 | 6/1989 | Doyle | 359/389 |
| 5,126,877 | 6/1992 | Biber | 359/389 |
| 5,345,333 | 9/1994 | Greenberg | 359/389 |
| 5,506,725 | 4/1996 | Koike et al. | 359/385 |
| 5,570,228 | 10/1996 | Greenberg | 359/389 |

FOREIGN PATENT DOCUMENTS

| | | | |
|---|---|---|---|
| 2052784 | 1/1981 | European Pat. Off. | 359/389 |
| U-9103433 | 6/1991 | Germany . | |
| 40 28 605 | 3/1992 | Germany . | |
| 92 17 517 | 4/1993 | Germany . | |
| U-9306412 | 6/1993 | Germany . | |
| 4214445 | 11/1993 | Germany . | |
| 4-86614 | 3/1992 | Japan | 359/385 |
| 2168167 | 6/1986 | United Kingdom | 359/385 |

Primary Examiner—Kenneth B. Wells
Attorney, Agent, or Firm—Foley & Lardner

[57] ABSTRACT

A switchable illumination system for a surgical microscope in eye surgery, which is provided with a light source, a collector lens system, a radiant field stop, optical deflecting elements, further lenses and a main objective. The radiant field stop is projected via the deflecting elements and the further lenses through the main objective onto the patient's eye to be viewed in the object plane. In the illumination beam there is provided a switching mechanism whereby the lamp filament of the light source is projected via the optical deflecting elements and the main objective onto the patient's eye to be viewed in the object planes.

7 Claims, 7 Drawing Sheets

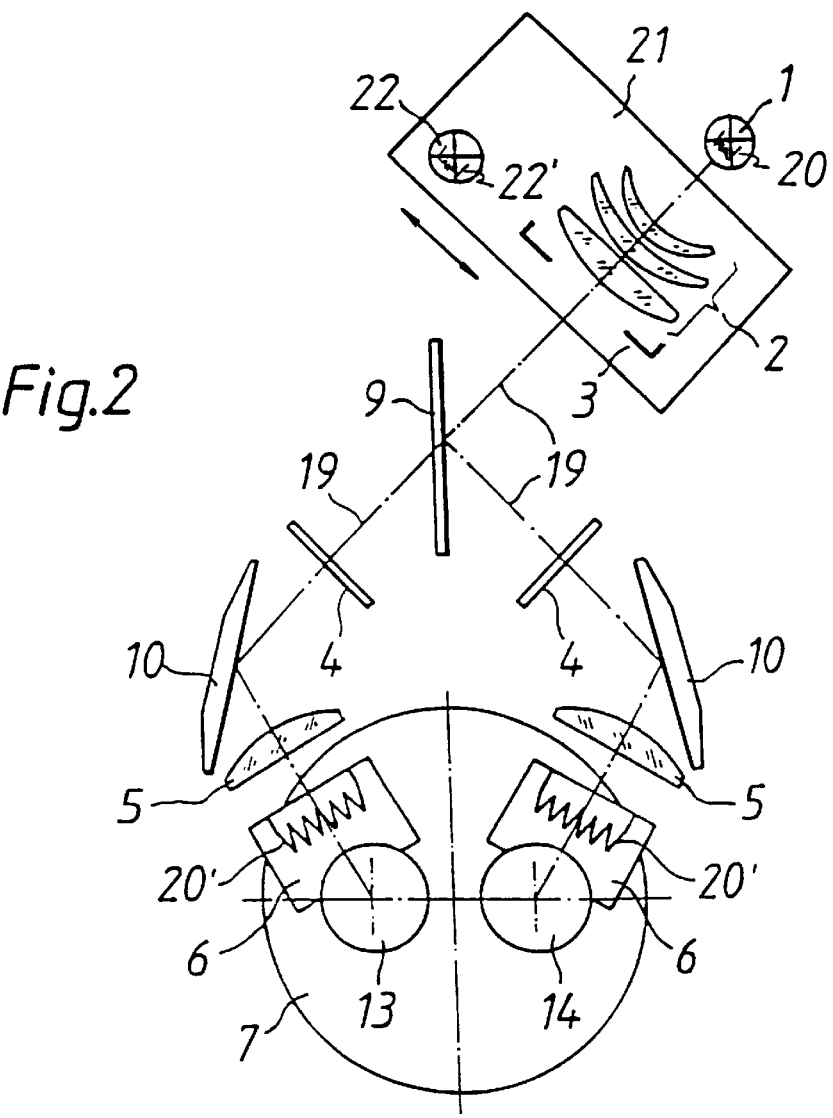
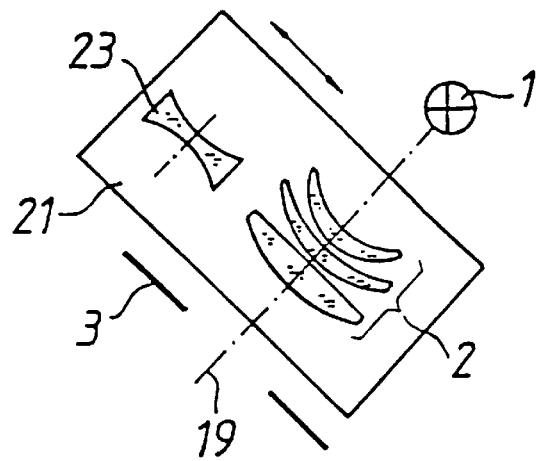

SWITCHABLE ILLUMINATION SYSTEM FOR A SURGICAL MICROSCOPE

BACKGROUND OF THE INVENTION

The invention relates to an illumination system for a surgical microscope, and more particularly to an illumination system which includes switchable illumination sources for use of the surgical microscope in eye surgery.

In the use of surgical microscopes in eye surgery, in particular in cataract extraction, the angle between the illumination axis and the observation axis of the microscope is to be kept as small as possible. An advantage of this type of illumination is that the light rays falling perpendicularly onto the eye are diffusely reflected by the retina and, as a result, the crystalline lens capsule of the eye appears as a reddish transmitted light. This effect is commonly referred to as a "red reflex". The quality of this red reflex is of particular significance in cataract extraction. In this operation, after initial removal of the lens of the eye all of the remaining tissue must be removed from the eye. This can only be accomplished if the remaining tissue can be accurately viewed, that is, illuminated with adequate optical contrast.

In the course of the operation, however, not only is the red-reflex representation required, but in addition, a conventional illumination, preferably a Köhler illumination, must also be used in order to illuminate the operating area Köhler illumination is a method of illuminating objects in which an image of the source is projected by a collector lens into the plane of the aperture diaphragm in the front focal plane of the condensers The condenser, in turn, projects an image of an illuminated field diaphragm at the opening of the collector into the object plane. In epi-microscopy (where the objective also serves as its own condenser) an aperture diaphragm is imaged by a relay lens into the back focal plane of the objective and the illuminated field diaphragm is arranged to be in a plane conjugate with that of the collector.

German Utility Model Patent DE 92 17 517 U1 describes one conventional surgical microscope with an illumination system by which a red-reflex representation of the crystalline lens capsule is made possible. In the described system, to increase the contrast for enhancing observation of a possible ametropia affecting the patient, an additional lens is swiveled into the beam between the main objective and close to the patient's eye. The illumination system described in this document has the disadvantage that the swiveling in of an additional lens between the operating site and the main objective reduces the operating space and consequently hinders the freedom of movement of the operating surgeon. Also, the complicated mechanical design means that there is no quick and uncomplicated switching over between the illumination of the operating area and the optimum creation of red reflex German published patent application DE 40 28 605 A1 discloses a red-reflex illumination system for a surgical microscope. The red reflex is achieved by reflecting only certain, near-axis illumination rays from the illumination beam in the direction of the main objective via specially designed deflecting elements. In such a system, due to the blocking out of illumination rays, a high light loss must be tolerated.

U.S. Pat. No. 4,657,357 discloses another conventional illumination system for a surgical microscope in which the illumination rays are passed via prisms near to the axis through the main objective. For this purpose, however, it is necessary to provide the main objective with recesses which are complex to produce thereby increasing the expense of the microscope.

In general, in the known surgical microscopes for eye surgery, the pupil appears red in the observation beam if the cone of rays of the illumination and the cone of rays of the observation intersect. However, the observation of the red reflex is made more difficult by the brightness outside the pupil and by disturbing reflections of the image of the lamp filament on the patient's retina.

SUMMARY OF THE INVENTION

It is therefore the object of the present invention to provide an illumination system of a surgical microscope with simple switching means for switching between desired illumination conditions during eye surgery. The desired illumination conditions may include both a Köhler illumination and an optimized red-reflex illumination or a combination of the two illuminations.

To achieve the above and other objects of the invention there is provided a surgical microscope suitable for use in eye surgery which includes: an illumination device, including a radiant field stop and at least one light source, for producing a light beam; an objective lens in the light path of the light beam, the objective lens producing a projection onto an object plane located at a position of the eye; and a switching unit, included in the illumination device, for selectively switching between desired illumination conditions. The illumination conditions include at least a first illumination condition having a projection of the radiant field stop at the object plane and a second illumination condition having a projection of a filament of a light source at the object plane.

The objects may be further achieved by providing a switchable illumination system for use in a surgical microscope in eye surgery, which includes a light source, a collector lens system, a radiant field stop, optical deflecting elements, and a main objective. The collector lens system, the radiant field stop, the optical deflecting elements, the additional lenses and the main objective define an illumination path. The radiant field stop is projected via the deflecting elements and the lenses through the main objective onto the object plane of the objective lens. The system further includes a switching mechanism operative to project the filament of the lamp used as the light source onto the object plane to achieve a desired lighting condition.

BRIEF DESCRIPTION OF THE DRAWINGS

The switchable illumination system for surgical microscopes according to the invention is better understood by reference to the following detailed description and to the accompanying figures, in which:

FIG. 2 shows the illumination beam in a plan view with an additional light source arranged on a slide;

FIG. 3 shows an exemplary embodiment according to FIG. 2 with a negative lens instead of the light source;

DETAILED DESCRIPTION OF THE PREFERRED EMBODIMENTS

In accordance with the instant invention, as revealed from experimentation, an optimized red reflex occurs if, instead of the radiant field stop or its conjugate plane, the image of the lamp filament of the light source is projected into the object plane to be viewed. This shifting of the imaging additionally achieves the advantageous effect that the portion of the eye outside the pupil is not illuminated. Furthermore, under such illumination conditions, no image of the lamp filament is produced on the retina of the eye and consequently stressing of the retina during the surgical operation can be minimized.

Figure 1:
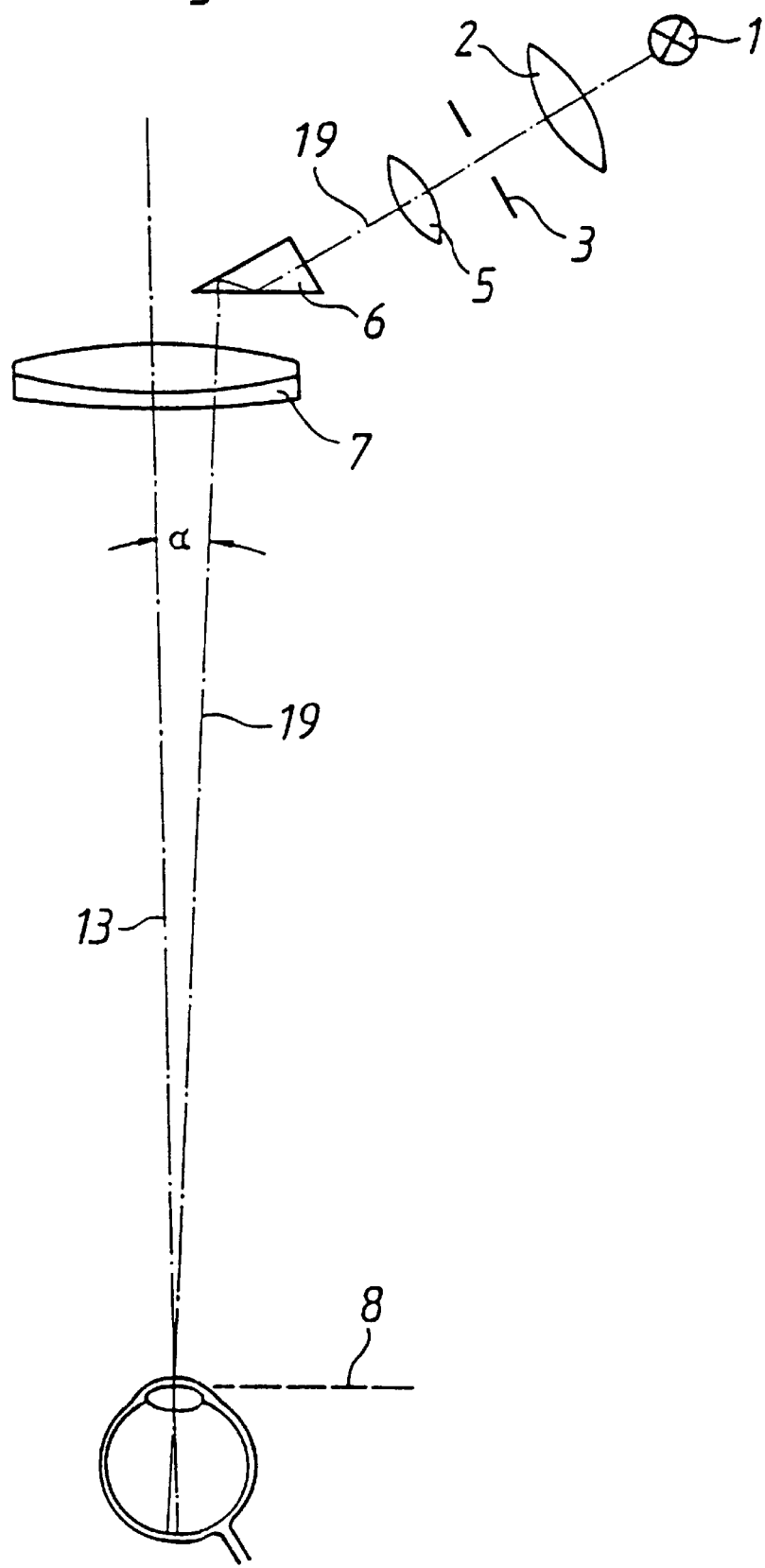
FIG. 1 shows the illumination beam in a sectional representation.

FIG. 1 shows a sectional representation through the illumination beam 19 of a microscope, in which the light of a light source 1 is passed via an optical system comprising a collector lens system 2, a radiant field stop 3, a further lens 5, a deflection prism 6, and a main objective 7 into an object plane 8. The beam 19 represented is formed as a Köhler illumination beam. In this case, the radiant field stop 3 is projected into the object plane 8 via the lens 5 and the objective 7. By means of an observation beam 13, the object or the object plane can be observed with the microscope (not shown in any more detail) as a bright image.

In this configuration, the illumination rays pass through the object plane 8 also onto the retina of the eye and, by scattering and reflection, usually produce a relatively weak and often unevenly luminous red reflex.

As already mentioned, the angle (alpha) between the observation beam 13 and the illumination beam 19 influences the intensity of the red reflex FIG. 2 shows the illumination beam 19 according to FIG. 1 in a plan view. For producing a stereoscopic illumination, the radiant field stop 3 is projected via a beam splitter 9, filters 4 arranged in the illumination beam 19, diathermic mirrors 10, lenses 5 and deflection prisms 6 through the main objective 7 into the object plane 8. In this optical arrangement, an intermediate image of the filament 20 of the light source 1 is simultaneously projected into the entry pupil of the main objective 7 (not shown). The intermediate image of the filament 20 is imaged via the main objective 7 onto the retina of the eye and a filament image 20' reflected from the retina of the eye is visible in the stereoscopic observation beams 13 and 14. To eliminate the above described disadvantages, in this exemplary embodiment the collector lens system 2 and the radiant field stop 3 are arranged on a slide 21, on which a further light source 22 is provided. This light source 22 can be brought into the illumination beam 19 by sliding (switching) the slide 21 such that the light source 22 is brought to the location of the radiant field stop 3 during the above-illumination. Additionally, the light source 1 can be shut off. In this arrangement, the lamp filament 22' of the light source 22 is then projected into the object plane 8, so that no sharp reflex image is produced on the retina. The specific stressing of the retina is reduced, since there is now homogeneous illumination. The imaging of the lamp filament 22' of the light source 22 in the object plane 8 additionally has the effect that objects outside the pupil are not illuminated, so that the contrast of the red reflex is increased.

FIG. 3 shows an exemplary embodiment in which there is arranged on the slide 21 in addition to the collector lens system 2 a negative lens 23. With a fixed light source 1 and radiant field stop 3, the imaging location of the lamp filament is changed by switching the slide 21 between a first position where the collector lens system 2 lies in the light source 1 beam path and a second position where the negative lens 23 lies in the path in a manner similar to that described in connection with FIG. 2.

Figure 4:
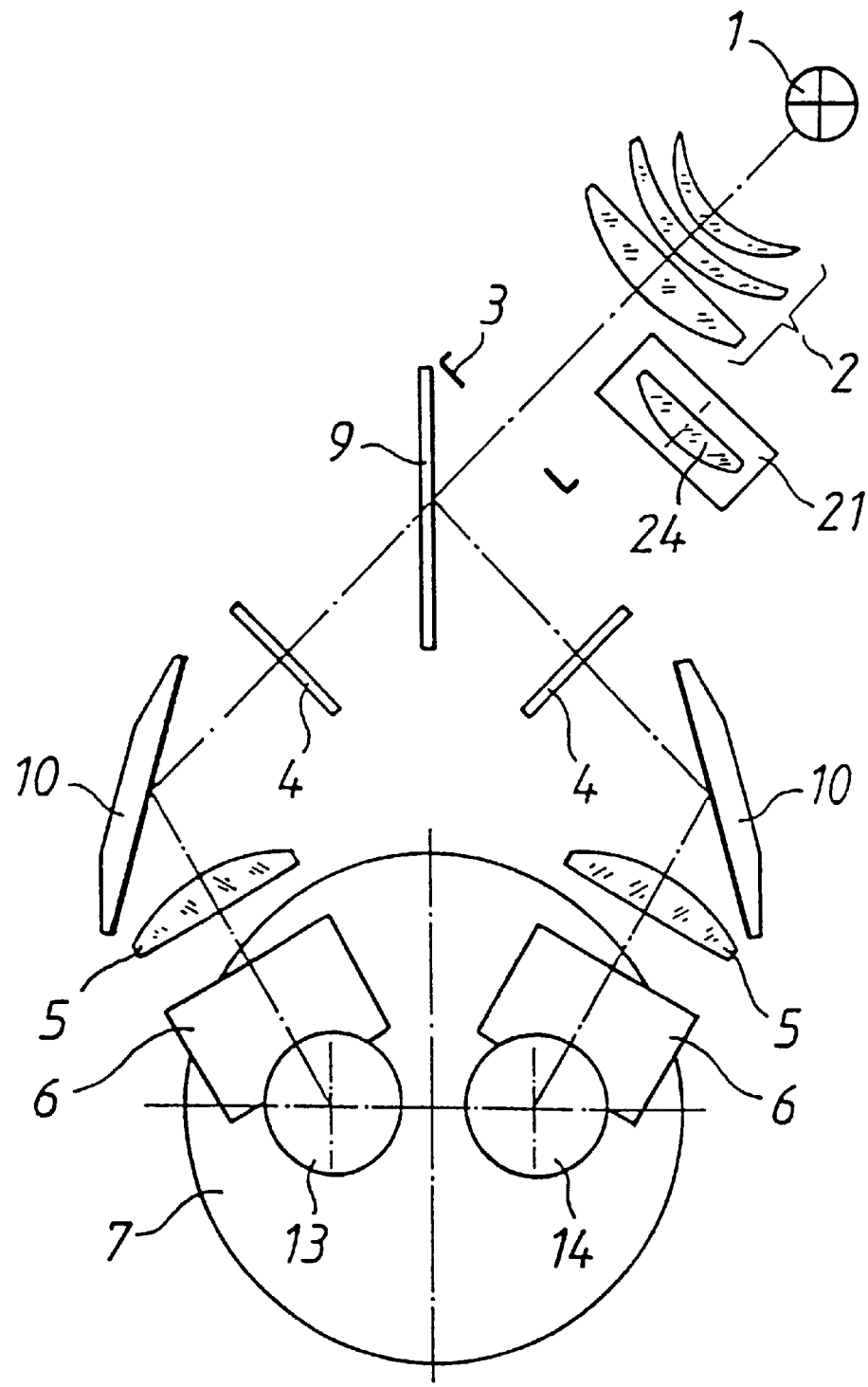
FIG. 4 shows a further exemplary embodiment with a positive lens arranged on a slide.

FIG. 4 shows an illumination arrangement similar to that of FIG. 2. In this embodiment, however, rather than switching the collector lens system 2 out of the beam path, the collector lens system 2 is supplemented by a positive lens 24, arranged on the slide 21, for selective insertion into the beam path to shift the filament image.

Figure 5:
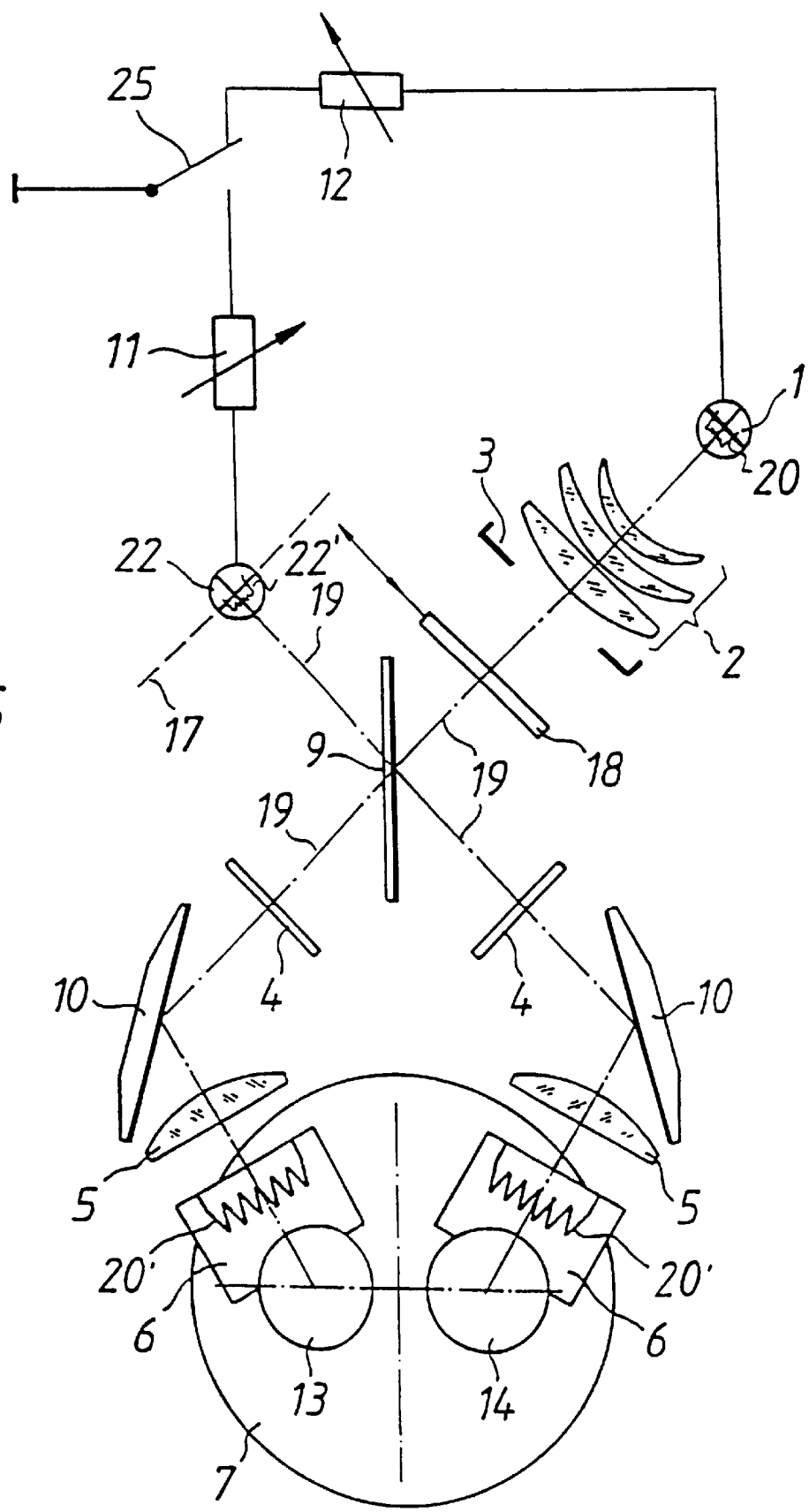
FIG. 5 shows an exemplary embodiment with an additional light source.
Figure 8:
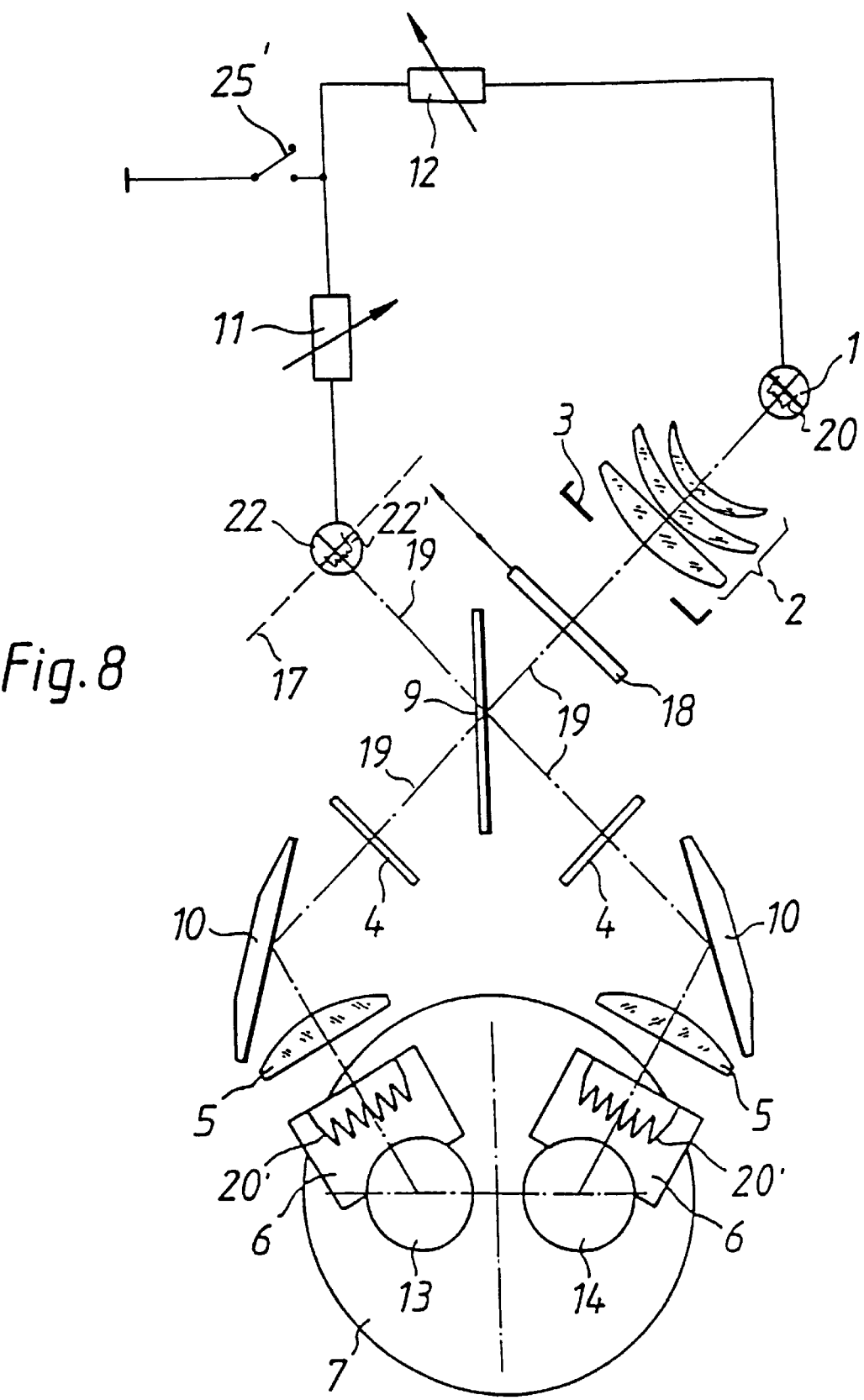
FIG. 8 shows an exemplary embodiment which produces two types of illumination at the same time.

FIG. 5 illustrates still another embodiment of the invention. In FIG. 5, an additional light source 22 is arranged in a plane 17 which is conjugate with respect to the radiant field stop 3. The light of this additional light source 22 is introduced into the illumination beams 19 via the beam splitter 9. For switching between desired illumination conditions, the light sources 1 and 22 are electrically connected to a switch 25, so that, according to the desired illumination, either of the light sources 1 or 22 can be activated. This switch may of course also be designed in such a way that both the light source 1 and the additional light source 22 are activated at the same time. Such an arrangement is shown in FIG. 8, which employs switch 25' to provide power to both light sources at the same time. This type of mixed illumination has the advantage that in addition to the production of improved red reflex, an illumination of the pupil periphery of the eye is also achieved. With this type of mixed illumination, the illumination intensity of the light source 1 is profoundly reduced. This can be performed, for example, by introducing a neutral density filter 18 into the portion of the illumination beam 19 emanating from light source 1. The electric circuit controlling the light sources 1 and 22 may also include potentiometers 11, 12, which may be used to control the corresponding lamp voltage and consequently the brightness of the light source.

The embodiment depicted in FIG. 5 is especially advantageous in that no mechanical or optical changes are required to switch between the desired illumination. The imaging of the lamp filament 22' in the object plane 8 achieves the effect that the angle between the illumination axis and the observation axis in red-reflex illumination is as small as possible, while in a Köhler illumination a larger angle is obtained for better three-dimensional perception of the object.

Figure 6:
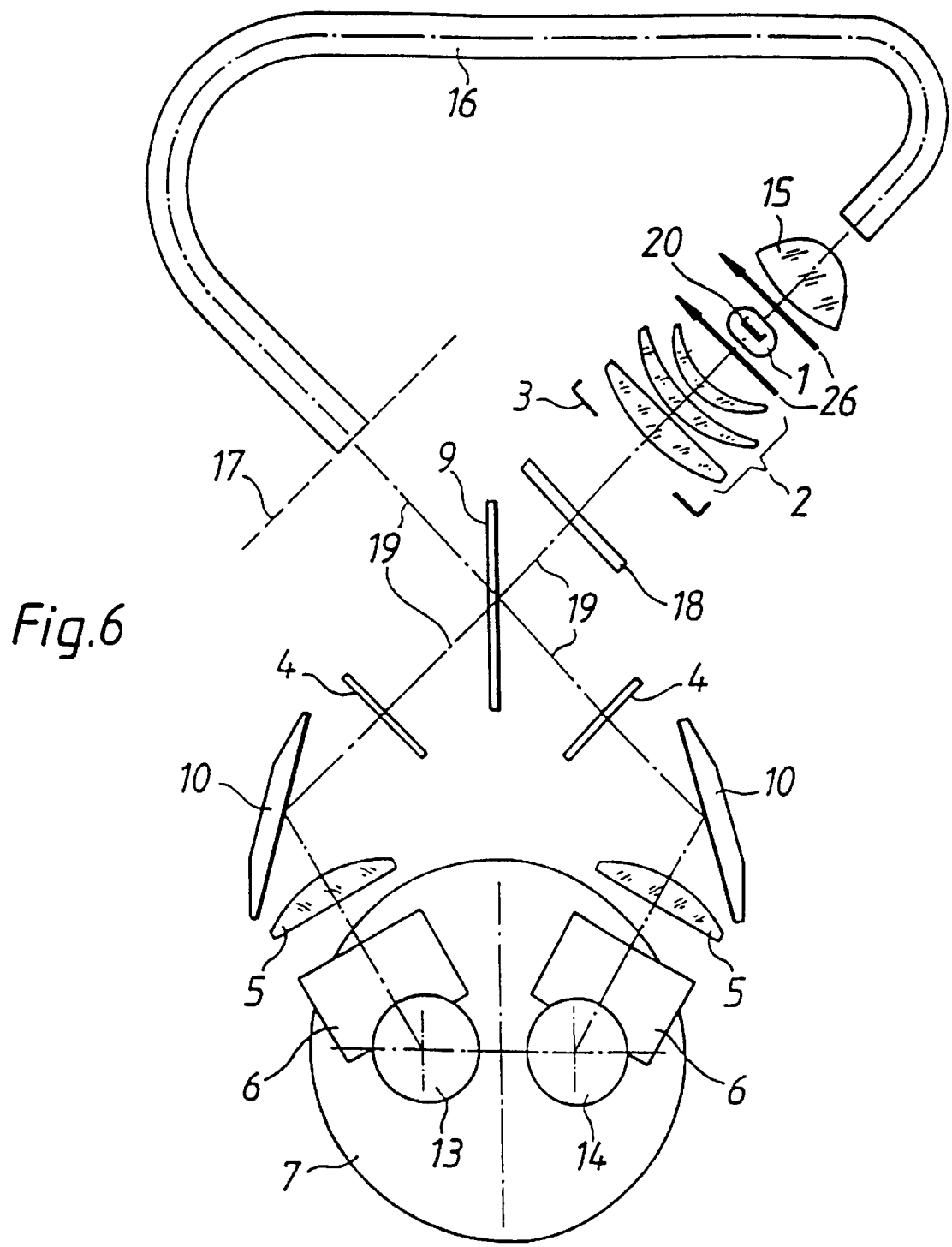
FIG. 6 shows an exemplary embodiment with a light guide and a common light source.

FIG. 6 shows another embodiment of the invention with a further collector lens 15 and a light guide 16. The light entry area of the light guide 16 faces the collector 15 and the light exit area is arranged in the plane 17 conjugate with respect to the radiant field stop 3. For switching between the desired illumination conditions, two light stops 26 are provided which can be inserted into the illumination beam 19. With the use of light guide 16, a suitable diameter size of the light spot on the eye can be appropriately chosen and adapted. Light stops 26 may be partially transmissive elements so as to permit simultaneous illumination via both optical path 16 and radiant field stop 3, the relative degree of illumination determined by the relative transmission characteristics of the elements 26.

Figure 7:
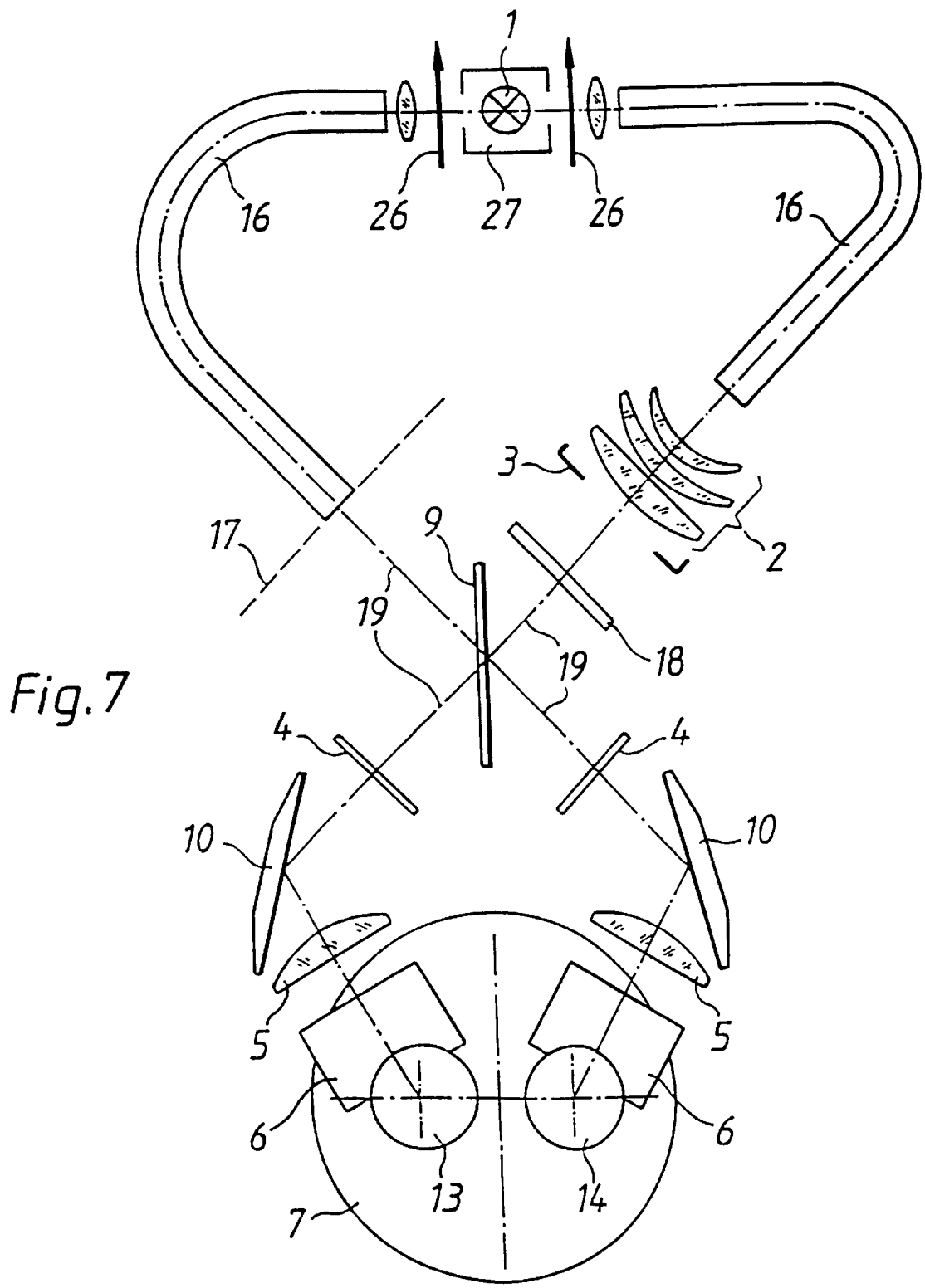
FIG. 7 shows an exemplary embodiment with an externally arranged light source.

FIG. 7 shows an embodiment similar to that of FIG. 6, but with a light source 1 arranged external to the microscope is a separate housing 27. The light source 1 is centrally located and emits light to a pair of light guides 16 arranged on respectively opposite sides of the housing. Between the lamp housing 27 and the light entry areas of the light guides 16, light stops 26 are provided for the switching between desired illumination conditions. As in the embodiment of FIG. 6, partially transmissive light element 26 may be used for simultaneous illumination via both guides 16.

In order to obtain both a red-reflex illumination and a Köhler illumination simultaneously, as already described with respect to the exemplary embodiment according to FIG. 5 or 6, the light stops 26 can also be partially introduced into the beam to appropriately control the intensity of the two illumination conditions.

The invention has been described in connection with the above embodiments. The invention is of course not restricted to the exemplary embodiments described. Many variations will be apparent to the skilled artisan on the basis of the above disclosure. For example, it is entirely within the scope of the invention to provide the manually described switching mechanisms with motorized means. It is also conceivable to design the electric switches in such a way that not only is the desired switching carried out but also the simultaneous operation of two light sources can be implemented. Accordingly, the instant invention is only limited by the appended claims.

What is claimed is:

1. A surgical microscope for use in surgery on an eye comprising:
    an illumination means, including a radiant field stop and a first light source, for producing light;
    an objective lens, which receives light from the illumination means, for producing a projection onto an object plane located at a position of the eye; and
    switching means, included in the illumination means, for selectively activating at least one of a plurality of illumination conditions that said surgical microscope produces, the illumination conditions including a first, Köhler, illumination condition having a projection of the radiant field stop at the object plane and a second, red reflex, illumination condition having a projection of a filament of said first light source at the object plane;
    wherein the illumination means further comprises
    a beam splitter; and
    a second light source and a collector lens system;
    wherein the first light source is arranged at a position conjugate to the radiant field stop, and
    wherein the second light source is used to produce the first illumination condition and the first light source is used to produce the second illumination condition.

2. A surgical microscope as recited in claim 1, further comprising means to adjust the intensity of said first and second light sources.

3. A surgical microscope as recited in claim 1, wherein said switching means permits simultaneous illumination of said first and second light sources to simultaneously produce said first and second illumination conditions.

4. A switchable illumination system for a surgical microscope in eye surgery, comprising:
    a first light source;
    a collector lens system;
    a radiant field stop;
    optical deflecting elements;
    additional lenses;
    a main objective;
    the collector lens system, the radiant field stop, the optical deflecting elements, the additional lenses and the main objective defining an illumination path and the radiant field stop being projected via the deflecting elements and the additional lenses through the main objective onto a patient's eye to be viewed in an object plane to produce Köhler illumination; and
    projecting means for projecting a lamp filament of the first light source onto the patient's eye to be viewed in the object plane to produce red reflex illumination; and further comprising
    a beam splitter located in the illumination path; and
    a second light source;
    wherein the first light source is arranged in a plane conjugate with respect to the radiant field stop, and
    wherein the system further includes a control means for controlling the illumination of the first light source and the second light source.

5. The system as recited in claim 4, wherein the projecting means includes means for simultaneously projecting both the radiant field stop and the lamp filament of the first light source via the deflecting elements and the additional lenses through the main objective onto the patient's eye to be viewed in the object plane.

6. The system as recited in claim 5, further comprising an intensity reducing filter arranged in the illumination path between the collector lens system and the beam splitter.

7. The system as recited in claim 4, wherein the control means comprises at least one potentiometer for controlling lamp voltage and consequently the brightness of the first light source and the second light source.

* * * * *